US 7,455,860 B2
Nov. 25, 2008

(12) United States Patent
Gokaraju et al.

(54) DIETARY SUPPLEMENT FORMULATION FOR CONTROLLING INFLAMMATION AND CANCER

(75) Inventors: Ganga Raju Gokaraju, Andhra Pradesh (IN); Rama Raju Gokaraju, Andhra Pradesh (IN); Venkata Subbaraju Gottumukkala, Andhra Pradesh (IN); Trimurtulu Golakoti, Andhra Pradesh (IN)

(73) Assignee: Laila Nutraceuticals, Andhra Pradesh (IN)

( * ) Notice: Subject to any disclaimer, the term of this patent is extended or adjusted under 35 U.S.C. 154(b) by 0 days.

(21) Appl. No.: 11/201,416

(22) Filed: Aug. 11, 2005

(65) Prior Publication Data

US 2006/0040000 A1 Feb. 23, 2006

(51) Int. Cl.
*A61K 36/00* (2006.01)
(52) U.S. Cl. .................................. 424/725; 424/774
(58) Field of Classification Search ............... None
See application file for complete search history.

(56) References Cited

U.S. PATENT DOCUMENTS

| | | | |
|---|---|---|---|
| 6,224,871 B1 * | 5/2001 | Hastings et al. | 424/195.17 |
| 6,492,429 B1 * | 12/2002 | Graus et al. | 514/688 |
| 7,112,343 B1 * | 9/2006 | Shoemake | 424/726 |
| 2004/0073060 A1 | 4/2004 | Gokaraju et al. | |
| 2004/0086581 A1 * | 5/2004 | Jones | 424/756 |
| 2004/0241256 A1 * | 12/2004 | Ehrenpreis et al. | 424/734 |

FOREIGN PATENT DOCUMENTS

WO    WO-03/074063 A1    9/2003

OTHER PUBLICATIONS

X. Z. Ding et al., "Cyclooxygenases and lipoxygenases as potential targets for treatment of pancreatic cancer", Pancreatology, vol. 1, 2001, pp. 291-299. (abstract).
N. Kimmatkar et al., "Efficacy and tolerability of *Boswellia serrata* extract in treatment of osteoarthritis of knee—A randomized double blind placebo controlled trial", Phytomedicine, vol. 10, 2003, pp. 3-7.
I. Gupta et al., "Effects of *Boswellia serrata* gum resin in patients with bronchial asthma: results of a double-blind, placebo controlled, 6-week clinical study", European Journal of Medical Research, vol. 3, 1998, pp. 511-514.
H. Gerhardt et al., "Therapy of active Crohn disease with *Boswellia serrata* extract H 15", Z Gastroenterol, vol. 39, 2001, pp. 11-17. (abstract).
H. Safayhi et al., "Anti-Inflammatory Actions of Pentacyclic Triterpenes", Planta Med., vol. 63, 1997, pp. 487-493.
H. Safayhi et al., "Boswellic Acids: Novel, Specific, Nonredox Inhibitors of 5-Lipoxgenase", Journal of Pharmacology and Experimental Therapeutics, vol. 261, 1992, pp. 1143-1146.
R. S. Pardhy et al., "β-Boswellic Acid, Acetyl-β-boswellic Acid, Acetyl-II-keto-β-boswellic Acid & II-Keto-β-boswellic Acid, Four Pentacyclic Triterpene Acids from the Resin of *Boswellia serrata* Roxb", Indian Journal of Chemistry, vol. 16B, 1978, pp. 176-178.
K. Hostanska et al., "Cytostatic and Apoptosis-inducing Activity of Boswellic Acids Toward Malignant Cell Lines In Vitro", Anticancer Research, vol. 22, 2002, pp. 2853-2862.
T. Syrovets et al., "Acetyl-Boswellic Acids Are Novel Catalytic Inhibitors of Human Topoisomerases I and IIα", Molecular Pharmacology, vol. 58, 2000, pp. 71-81.
M. L. Sharma et al., "Immunomodulatory Activity of Boswellic Acids (Pentacyclic Triterpene Acids) from *Boswellia serrata*", Phytotherapy Research, vol. 10, 1996, pp. 107-112.
E. R. Sailer et al., "Acetyl-11-keto-β-boswellic acid (AKBA): structure requirements for binding and 5-lipoxygenase inhibitory activity", British Journal of Pharmacology, vol. 117, 1996, pp. 615-618.
E. R. Sailer et al., "Characterization of an acetyl-11-keto-β-boswellic acid and arachidonate-biding regulatory site of 5-lipoxygenase using photoaffinity labeling", Euro. J. Biochem, vol. 256, 1998, pp. 364-368.
T.E. Towheed, "Current status of glucosamine therapy in osteoarthritis," Arthritis Rheum., vol. 49, 2003, pp. 601-604.
A. L. Vas, "Double-blind clinical evaluation of the relative efficacy of ibuprofen and glucosamine sulphate in the management of osteoarthrosis of the knee in out-patients", Curr. Med. Res. Opin., vol. 8, 1982, pp. 145-149. (abstract).
E. D'Ambrosio et al., "Glucosamine sulphate: a controlled clinical investigation in arthrosis", Pharmatherapeutica, vol. 2, 1981, pp. 504-508. (abstract).
M. J. Tapadinhas et al., "Oral glucosamine sulphate in the management of arthrosis: report on a multi-centre open investigation in Portugal", Pharmatherapeutica, vol. 3, 1982 pp. 157-168. (abstract).
C. Natarajan et al., "Curcumin Inhibits Experimental Allergic Encephalomyelitis by Blocking IL-12 Signaling Through Janus Kinase-STAT Pathway in T Lymphocytes", The Journal of Immunology, vol. 168, 2002, pp. 6506-6513.
R. R. Satoskar et al., "Evaluation of anti-inflammatory property of curcumin (diferuloyl methane) in patients with postoperative inflammation", Int. J. Clin. Pharmacol. Ther. Toxicol., vol. 24, 1986, pp. 651-654. (abstract).
L. Dalton, "How Curry Combats Cancer", C&EN, vol. 81, 2003, p. 8.
S. J. Taussig, "The mechanism of the physiological action of bromelain", Medical Hypotheses, vol. 6, 1980, pp. 99-104. (abstract).
H. Ako et al., "Isolation of a fibrinolysis enzyme activator from commercial bromelain", Arch. Int. Pharmacodyn. Ther., vol. 254, 1981, pp. 157-167. (abstract).
G.H. Tilwe et al., "Efficacy and tolerability of oral enzyme therapy as compared to diclofenac in active osteoarthritis of the knee joint: an open randomized controlled clinical trial," Journal of the Association of Physicians of India, vol. 49, 2001, pp. 617-621.

(Continued)

*Primary Examiner*—Christopher R Tate
*Assistant Examiner*—Deborah A. Davis
(74) *Attorney, Agent, or Firm*—Radar, Fishman & Grauer, PLLC

(57) ABSTRACT

This invention relates to a dietary supplement which is a phytochemical composition. This composition is capable of controlling inflammatory conditions and preventing and curing cancer in mammals. The composition comprises a synergistic mixture of standardized *Boswellia* extract, salts of glucosamine, and curcuminoids optionally containing bromelain, chondroitin, methylsulphonylmethane, resveratrol, extracts of white Willow and ginger, and quercetin.

14 Claims, No Drawings

OTHER PUBLICATIONS

Monograph, "Methylsulfonylmethane (MSM)", Alternative Medicine Review, vol. 8, 2003, pp. 438-441.

M. A. Beilke et al., "Effects of dimethyl sulfoxide on the oxidative function of human neutrophils", J. Lab. Clim. Med., vol. 110, 1987, pp. 91-96. (abstract).

D. L. Layman, "Growth inhibitory effects of dimethyl sulfoxide and dimethyl sulfone on vascular smooth muscle and endothelial cells in vitro", In Vitro Cell Dev. Biol., vol. 23, 1987, pp. 422-428. (abstract).

J. I. Morton et al., "Effects of oral dimethyl sulfoxide and dimethyl sulfone on murine autoimmune lymphoproliferative disease", Proc. Soc. Exp. Biol. Med., vol. 183, 1986, pp. 227-230. (abstract).

S. J. Childs, "Dimethyl sulfone (DMSO2) in the treatment of interstitial cystitis", Urol. Clin. North Am., vol. 21, 1994, pp. 85-88. (abstract).

E. Barrager et al., "A multicentered, open-label trial on the safety and efficacy of methylsulfonylmethane in the treatment of seasonal allergic rhinitis", J. Alterm Compliment Med., vol. 8, 2002, p. 229. (abstract).

P. R. Usha et al., "Randomised, Double-Blind, Parallel, Palacebo-Controlled Study of Oral Glucosamine, Methylsulfonylmethane and their Combination in Osteoarthritis", Clinical Drug Investigation, vol. 24, 2004, pp. 353-363. (abstract).

D. Bagchi., "Resveratrol and Human Health", Keats Publishing, Los Angeles, 2000.

M. Maccarrone et al., "Resveratrol prevents apoptosis in K562 cells by inhibiting lipoxygenase and cyclooxygenase activity", Eur. J. Biochem., vol. 265, 1999, pp. 27-34.

J. Martinez et al., "Effect of resveratrol, a natural polyphenolic compound, on reactive oxygen species and prostaglandin production", Biochem. Pharmacol., vol. 59, 2000, pp. 865-870. (abstract).

B. Schmid et al., "Efficacy and tolerability of a standardized willow bark extract in patients with osteoarthritis: randomized placebo-controlled, double blind clinical trial", Phytother Res., vol. 15, 2001, pp. 344-350. (abstract).

E. Tjendraputra et al., "Effect of ginger constituents and synthetic analogues on cyclooxygenase-2 enzyme in intact cells", Bioorg. Chem., vol. 29, 2001, pp. 156-163. (abstract).

K. C. Srivastava et al., "Ginger (Zingiber officinale) in rheumatism and musculoskeletal disorders", Med. Hypotheses, vol. 39, 1992, pp. 342-348. (abstract).

D. Loggia et al., "Anti-inflammatory activity of benzopyrones that are inhibitors of cyclo- and lipo-oxygenase", Pharmacol. Res. Commun., vol. 20, 1988, pp. 91-94. (abstract).

H. P. Kim et al., "Effects of naturally-occurring flavonoids and biflavonoids on epidermal cyclooxygenase and lipoxygenase from guinea-pigs", Prostaglandins Leukotrienes and Essential Fatty Acids, vol. 58, 1998, pp. 17-24. (abstract).

C. C. Fox et al., "Comparison of human lung and intestinal mast cells", J. Allergy Clin. Immunol, vol. 81, 1988, pp. 89-94. (abstract).

C. Bronner et al., "Kinetics of the inhibitory effect of flavonoids on histamine secretion from mast cells", Agents Actions, vol. 16, 1985, pp. 147-151. (abstract).

A. Ristimaki, "Cyclooxygenase 2: from inflammation to carcinogenesis", Novartis Found Symp., vol. 256, 2004, pp. 215-221; discussion pp. 221-226, 259-269. (abstract).

H. Zhi et al., "The deregulation of arachidonic acid metabolism-related genes in human esophageal squamous cell carcinoma", Int. J. Cancer, vol. 106, 2003, pp. 327-333. (abstract).

D. Pereg et al., "Non-steroidal anti-inflammatory drugs for the prevention and treatment of cancer", J. Intern Med., vol. 258, 2005, pp. 115-123. (abstract).

M. Coles et al., "Prevention of tumors of the large intestine by celecoxib in mice", In Vivo., vol. 19, 2005, pp. 661-665. (abstract).

R. Kuttan et al., "Potential anticancer activity of turmeric (Curcuma longa)", Cancer Lett., vol. 29, 1985, pp. 197-202. (abstract).

B. B. Aggarwal et al., "Role of resveratrol in prevention and therapy of cancer: preclinical and clinical studies", Anticancer Res., vol. 24, 2004, pp. 2783-2840. (abstract).

Y. Jing et al., "Boswellic acid acetate induces differentiation and apoptosis in leukemia cell lines", Leukemia Research, vol. 23, 1999, pp. 43-50.

J. L. McLaughlin et al., "The use of biological assays to evaluate botanicals," Drug Information Journal, vol. 32, 1998, pp. 513-524.

J.L. Blonstein, "Control of Swelling in Boxing Injuries," The Practitioner, vol. 203, 1969, pp. 206.

T.L Ratliff, "High Molecular Mass Proteome of Androgen-Independent Prostate Cancer," J. Urol., vol. 174, 2005, p. 787.

S.W. Jacob, "The Definitive Guide. A Comprehensive Review of the Science and Therapeutics of Methylsulfonoylmethane," Freedom Press, 2003, pp. 107-121. (abstract).

R.C. Srimal, "Pharmacology of Differuloyl Methane (Curcumin), a Non-Steroidal Anti-Inflammatory Agent," Pharm. Pharmacol, vol. 25, 1973, pp. 447-452. (abstract).

A.W. Opher, "The Inhibition of Bromelain," Exp. Med. Surg., vol. 25, 1967, pp. 185-191. (abstract).

F. Pirotta, "Bromelain: A Deeper Pharmacologic Study," Exp. Clin. Res., vol. 4, 1978, pp. 1-20. (abstract).

B. Seligman, "Bromelain: An Anti-inflammatory Agent," Angiology, vol. 13, 1962, pp. 508-510. (abstract).

W.I. Cox, "Susceptibility of Friend Erythroleukemia Cells to Natural Cytotoxicity After In Vitro Treatment with Dimethyl Sulfoxide," Proc. Soc. Exp. Biol. Med., vol. 169, 1982, pp. 337-342. (abstract).

\* cited by examiner

DIETARY SUPPLEMENT FORMULATION FOR CONTROLLING INFLAMMATION AND CANCER

FIELD OF THE INVENTION

The present invention relates to new dietary supplement compositions comprising 5-LOXIN, glucosamine hydrochloride and curcuminoids, and optionally bromelain, chondroitin, methylsulfonylmethane, resveratrol, white Willow (*Salix alba*), ginger, and quercetin.

BACKGROUND OF THE INVENTION

Inflammation is a critical protective biological process triggered by irritation, injury or infection, characterized by redness and heat (due to increased blood flow), swelling (due to increased vascular permeability), loss of function and pain (due to sensitization of pain receptors). In addition to the foregoing induced conditions, inflammation can also occur due to age related factors. The life expectancy of general population has increased dramatically during the past few decades due to the efficient control of the infectious diseases and better access to nutritious food. This positive enhancement in life span coupled with changing environmental conditions elevated the incidence of chronic age-related diseases such as arthritis, diabetes, cancer, cardiovascular diseases, etc. Chronic inflammatory conditions and cancer have become emerging health concerns in a number of countries across the globe and for people among all cultures. Arthritis is one of the most debilitating diseases of modern times. The quality of life for sufferers of these two diseases and their families is severely affected. Non-steroidal anti-inflammatory drugs are most commonly used remedies for rheumatic diseases. Presently, there has been a tremendous surge in demand for natural non-steroidal antiinflammatory drugs (NSAIDs) because of their established safety and efficacy, through decades of usage by various cultures.

The inflammatory and carcinogenesis processes are known to be triggered by increased metabolic activity of arachidonic acid. Arachidonic acid diverges down into two main pathways during this process, the cyclooxygenase (COX) and lipooxygenase (LOX) pathways. The COX pathways lead to prostaglandin and thromboxane production and the LOX pathways leads to leukotrienes (LTS) and 5(S)-hydroxy-6,8,11,14-E,Z,Z,Z-eicosatetraenoic acid [5(S)-HETEs]. These classes of inflammatory molecules exert profound biological effects, which enhance the development and progession of human cancers (Ding, X. Z., et. al., *Pancreatology*. 2001; 1(4):291-9).

Leukotrienes and 5(S)-HETE are important mediators for inflammatory, allergic and obstructive process. Leukotrienes increase microvascular permeability and are potent chemotactic agents. Inhibition of 5-lipooxygenase indirectly reduces the expression of TNF-α (a cytokine that plays a key role in inflammation). 5-Lipoxygenase is therefore the target enzyme for identifying inhibitors, which have potential to cope with a variety of inflammations and hypersensitivity-based human diseases including asthma, arthritis, bowel diseases such as ulcerative colitis and circulatory disorders such as shock and ischaemia.

Similarly prostaglandins are intercellular messengers that are produced in high concentration at the sites of chronic inflammation and are capable of causing vasodilation, increased vascular permeability and sensitizing pain receptors. The pro-inflammatory prostaglandins (PGE2) are produced by inducible isoform cyclooxygenase-2 (COX-2). The prostaglandins that are important in gastrointestinal and renal function are produced by the constitutively expressed isoform, cyclooxygenase-1 (COX-1). COX-1 is the protective housekeeper isoform and it regulates mucosal cell production of mucous that provides a barrier between the acid and pepsin present in gastric secretions. Non-selective COX inhibitors thus produce serious side effects. Scientists around the world are thus investing a major effort in identifying non-steroidal anti-inflammatory drugs that inhibit 5-lipoxygenase and cyclooxygenase-2 enzymes. As both COX-2 and 5-LOX are commonly expressed in any kind of inflammatory condition, efforts are currently being focused to obtain the so called dual acting anti-inflammatory drugs that are able to inhibit both COX-2 and 5-LOX enzymes. Unfortunately, the odds of finding a new dual acting natural NSAID that can truly alleviate the symptoms of inflammatory diseases are very thin. Hence, the researchers conceived the idea that using a combination of drugs, one having the COX-2 inhibitory activity and the other having 5-LOX inhibitory activity, as the next best option.

Rheumatoid arthritis is a chronic inflammatory condition that affects the lubricating mechanism and cushioning of joints. As a result of this autoimmune disease the bone surfaces are destroyed, which leads to stiffness, swelling, fatigue and crippling pain. Osteoarthritis is the common form of arthritis and results primarily from progressive degeneration of cartilage glycoaminoglycons. The damage is often compounded by a diminished ability to restore and repair joint structures including cartilage. The smooth surface of the cartilage becomes hard and rough, creating friction. As a result of this, the joint gets deformed, painful and stiff. Studies have indicated that over 40 million Americans have osteoarthritis, including 80% of persons over the age of 50. The major focus for osteoarthritis treatment, should therefore involve agents that not only stimulate the production of biological substances necessary for regeneration of cartilage cells and proper joint function but also diminish pain inflammation.

It is therefore an object of the present invention to provide a non-toxic supplement, which exhibits anti-arthritic and anti-inflammatory properties without deleterious side effects.

It is also an object of the present invention to provide a composition, which is useful both as an anti-cancer agent and anti-oxidant.

DISCLOSURE OF THE INVENTION

The present invention provides new dietary supplement compositions, comprising 5-Loxin, glucosamine hydrochloride, curcuminoids and optionally bromelain, chondroitin, methylsulfonylmethane, resveratrol, white Willow (*Salix alba*), ginger, and quercetin. The claimed dietary supplement is useful as a nutritional supplement, anti-inflammatory agent and an antioxidant.

5-Loxin

Gum resin of *Boswellia* species known as Indian frankincense has been used as an anti-inflammatory agent in Traditional Ayurvedic Medicine in India. Ancient Ayurvedic texts described its therapeutic use. Clinical trails performed by CSIR laboratories in India have shown fair to excellent results in 88% of the patients, with no adverse side effects [Singh, G. B., *Status report, anti-inflammatory drugs from plant sources* (1982)]. A randomized, double blind, placebo controlled clinical trials on patients with Osteoarthritis of knee exhibited statistically significant reduction in pain, decreased swelling and increased knee flexion etc. [*Kimmatkar, Phytomedicine* 10: 3-7 (2003)]. The therapeutic effects shown by *Boswellia serrata* extract were comparable to those exhibited by sulfasalazine and mesalazine in patients with ulcerative colitis. (Gupta, I., et al., *Eur. J. Med. Res.*, 3: 511-14, 1998 and Gerhardt, H., et. al., *Gastroenterol.*, 39: 11-17, 2001). The source of anti-inflammatory actions has been attributed to a group of triterpene acids called boswellic acids (Safayhi, H., et al., *Planta Medica* 63, 487-493, 1997 and *J. Pharmacol. Exp. Ther.* 261, 1143-46, 1992, both the journals published from USA), isolated from *Boswellia* resin (Pardhy, R. S., et al., *Indian J. Chem.*, 16B, 176-178, 1978). These compounds exert anti-inflammatory activity by inhibiting 5-lipoxygenase (5-LO). Apart from having anti-inflammatory actions, the boswellic acids also gained prominence recently for their antiproliferative actions. Boswellic acid inhibited several leukemia cell lines in vitro and inhibited melanoma growth and induced apoptosis (Hostanska, K., et al., *Anticancer Res.*, 22(5), 2853-62, 2002). The acetyl boswellic acids were found to be unique class of dual inhibitors of human topoisomerages I and II α (Syrovets, T. et al. *Mol. Pharmacol.* 58 (1), 71-81, 2000). Immunomodulatory activity of boswellic acids had been reported by Sharma et al. in *Phytotheraphy Research*, (10, 107-112, 1996), published from USA. A detailed study on the structural requirements for boswellic acids indicated that, of all the six acids, 3-O-acetyl-11-keto-β-boswellic acid, hereinafter referenced as AKBA shows most pronounced inhibitory activity against 5-LO (Sailer, E. R., et al., *British J Pharmacology*, 117, 615-618, 1996). AKBA acts by unique mechanism, in which it binds to 5-LO in a calcium-dependent and reversible manner and acts as a non-redox-type, non-competitive inhibitor (Sailer, E. R., et al., *Euro. J. Biochem.*, 256, 364-368, 1998). AKBA has thus become the subject of intensive research for its potential for the treatment of chronic inflammatory disorders. Efforts are currently being made to enrich AKBA in the natural extracts and also to synthesize structural analogs of AKBA to enhance the efficacy and water solubility.

The enrichment of AKBA to 10 to 100% from natural *Boswellia* extract has already been undertaken by the inventors and described in international patent application (PCT # WO 03/074063, dtd. 12 Sep. 2003) and US patent application. (Appl. # 20040073060, dtd. 15 Apr. 2004). 5-LOXIN is the brand name for a *Boswellia* extract having not less than 30% AKBA. Product enriched at higher levels of AKBA may also be used.

Glucosamine

Glucosamine is a natural substance found in high quantities in joint structures. The main function of glucosamine in joint structures is to produce cartilage components necessary for maintaining and repair joint tissue. Glucosamine stimulates the formation of joint structural components such as collagen, the protein of the fibrous substances that holds the joints together and helps to build-up the cartilage matrix. Collagenis the main component of the shock-absorbing cushion called articular cartilage. It is also a necessary nutrient in the production of synovial fluid. Some people may lose the ability with age to produce glucosamine, thereby inhibiting the growth of cartilage destroyed during wear and tear in osteoartritis patients (Towheed, T. E., *Arthritis and and Rheumatism*, 49, 601-604, 2003). When taken orally as a dietary supplement in the form of glucosamine sulfate, it has been shown to exert protective effect against joint destruction and is selectively used by joint tissues to promote healthy joint function and show potential therapeutic effect in osteoarthritis (Perry, G. H., et al., *Ann. Rheum. Dis.*, 31,440-448, 1972).

Several double-blind studies with glucosamine sulfate showed therapeutic effects comparable to or even better than non steroidal anti-inflammatory drugs in relieving the symptoms of osteoarthritis (Vaz, A. L., *Curr. Med. Res. Opin.*, 8, 145-149, 1982; D'Ambrosia, E. D., et al., *Pharmatherapeutica*, 2, 504-508, 1982 and Tapadinhas, M. J., et al., *Pharmatherapeutica*, 3, 157-168, 1982). The NSAIDs offer only symptomatic relief, whereas glucosamine addresses the root cause of osteoarthritis disease. It support body's natural ability to tackle the disease on its own by providing the building blocks to many structural components such as glucosaminoglycons to repair the damage caused by osteoartritis. Glucosamine hydrochloride is used for this study.

Other forms of glucosamine, like, glucosamine sulfate or N-acetyl glucosamine could be used for this composition.

Curcuminoids

Curcumins, are key components of culinary delight, tumeric (*Curcuma longa*). The rhizome of this plant has been traditionally used as an anti-inflammatory agent in Ayurvedic medicine. The clinical trials have established that curcumins are significantly active as anti-inflammatory and analgesic agents. Curcumin has been effective in reducing the inflammation in both chronic and acute conditions (Srimal, R. C., et al., *J. Pharmacol.*, 25, 447-452, 1973) and it also acts as a nerve-protecting agent (Natarajan, C., et. al., *J. Immunol.*, 168, 6506-6513, 2002). In a double-blind study, curcumin exhibited therapeutic efficacy comparable to phenylbutazone in patients with rheumatoid arthritis, and produced significant improvements in the duration of morning stiffness, walking time and joint swelling (Deodhar, S. D., et al., *Indian J. Med. Res.*, 71, 632-634, 1980). Curcumins also reduced inflammations in surgical patients (Satoskar, R. R., et. al., *Int. J. Clin. Pharmacol. Ther. Toxicol.*, 24, 651-654, 1986). Further, curcumins showed in an animal study, lower ulcerogen index (0.6) than a similar dose of phenylbutazone. The in vitro studies have indicated that curcumins inhibit the expression and activity of cyclooxygenase (COX-2) and 5-lipooxygenase (5-LOX) enzymes. They have been shown to inhibit the formation of leukotriene (a major inflammatory mediator) and proinflammatory prostaglandins, inhibit platelet aggregation and neutrophil formation, and stabilize lysosomal membranes. Curcumin has also been shown to have antioxidant, cholesterol lowering, hepatoprotective, carmative, and antimicrobial antitumoural abilities. Curcumin is currently in phase I clinical studies for the treatment of colon cancer (Dalton, L., *C&E News*, 81(35): 8, 2003. Curcuminoids (95%) was used in this study.

Bromelain

Bromelain is a proteolytic enzyme extracted from pineapple. It is thought to modulate the arachidonate cascade reducing the body's production of pro-inflammatory prostaglandins (Taussig, S. J., *Med. Hypoth.*, 6, 99-104, 1980) and may support the body in reducing the pain associated with aging and inflamed joints. Pharmacological studies indicate that bromelain inhibits platelet aggregation and this may explain its anti-inflammatory activity. Another mechanism for its actions appears to involve its interaction with fibrin, a substance that collects in areas of inflammation and leads to swelling and pain. Bromelain lyses the fibrin accumulated and reduce the inflammation. (Ako, H., et al., *Arch. Int. Pharmacodyn.*, 254, 157-167, 1981). A vast number of clinical trials indicated its effectiveness against inflammation and edema (Miller, J. M., et al., *Exp. Med. Surg.*, 22, 293-299, 1964; Pirotta, F. et al., *Drugs Exp. Clin. Res.* 4, 1-20, 1978. Tassman, G. C., et. al., *J. Dent. Med.*, 19, 73-77, 1964; Tilwe, G. H., et al., *J. Assoc. Phys. India*, 49, 617-621, 2000). In a controlled study, inflammations caused from boxing injuries cleared faster in bromelain treatment group than in a group treated with placebo (Blonstein, J., *Practioner*, 203, 206, 1960). In a single (Seltzer, A. P., *EENT monthly,* 41, 813-817, 1962) and double-blinded (Tassman, G. C., et. al., *J. Dent. Med.,* 20, 51-54, 1965) studies, bromelain reduced the inflammation caused from surgery. Bromelain is effective in all inflammatory conditions, regardless of etiology, including those in physical trauma, infectious agents, surgical procedures, immunological reactions and prostaglandin metabolism, burns, phlebitis and cellulites (Pizzorno, J. E., *A Text Book of Natural Medicine, Bromelain.* John Bastyl College Publications, Seattle, V: Bromel 1-Bromel 5, 1987; Cirelli, M. G., *Delaware Med. J.,* 34, 159-167, 1962; Seligman, B., *Angiology,* 13, 508-510, 1962).

Methylsulfonylmethane (MSM)

Methylsulfonylmethane (MSM) is an organosulfur compound that occurs naturally in a broad range of plants and mammals including fruits, vegetables, grains, animals and humans. It is an oxidative metabolite of dimethylsulfoxide (DMSO). Its potential therapeutical significance was manifested by an array of in vivo and in vitro and positive outcome from clinical trials for certain pathologies (Monograph, Alternative *Medicine Review,* 8(4), 438-441, 2003). MSM was shown to have anti-inflammatory and antioxidant (Beilke, M. A., et al., *J. Lab. Clin. Med.,* 110, 91-96, 1987) and chemopreventive (COX, W. I., et al., *Proc. Soc. Exp. Biol. Med.,* 169, 337-342, 1982) properties in vitro systems. It has shown dose dependant suppression of growth and proliferation of cultured aortic smooth muscle and endothelial cells (Layman, D. L., *In Vitro Cell Dev Biol.,* 23, 422-428, 1987). MSM inhibited spontaneous autoimmune reactions, such as lymphoproliferative diseases in animals and it was quite effective in reducing enlargement of spleen, thymus and lymph nodes (Morton, J. I., et al., *Proc. Soc. Exp. Biol. Med.,* 183, 227-230, 1986).

MSM was reported to be effective as a treatment for interstitial cystitis disease (Childs, S. J., Urol. Clin. North Am., 21, 85-88, 1994) in reducing the pain and inflammation (Jacob, S. W., Appleton, J., Eds MSM: *The Definitive Guide. A Comprehensive Review of the Science and Therapeutics of Methylsulfonylnethane,* Topanga, Calif., Freedom Press, pp 107-121, 2003). In a multi-centered, open-label trial, MSM greatly reduced allergy symptoms in individuals suffering from seasonal allergic rhinitis (Barrager, E., *J. Altern Complement. Med.,* 8, 167-173, 2002). In a double blind study conducted by Lawrence et. al., MSM has shown 80% improvement in degenerative arthritis in treatment group, compared to 20% in placebo group and it has also been used clinically to treat conditions such as snoring, scleroderma, fibromyalgia, systemic lupus, erythematosus, repetitive stress injuries and osteoarthritis (Jacob, S. W., Appleton, J., Eds MSM: *The Definitive Guide. A Comprehensive Review of the Science and Therapeutics of Methylsulfonylmethane,* Topanga, Calif., Freedom Press, pp 107-121, 2003). It was observed in a recent clinical study that the combination of methylsulfonylmethane with glucosamine provides better and more rapid improvement, than either agent alone, in patients with osteoarthritis (Clinical Drug Investigations, June 2004). In addition to all the forgoing health benefits, MSM was found to be safe and well tolerated and the existing toxicological data suggest that MSM is nontoxic.

Chondroitin

Chondroitin is high viscosity mucopolysaccharides with N-acetylchondrosine as a repeating unit and one sulfate group per saccharide unit. These biological polymers act as the flexible connecting matrix between the tough protein filaments in cartilage to form a polymeric system similar to reinforced rubber. Chondroitin 4-sulfate chondroitin 6-sulfate are the most abundant mucopolysaccharides in the body and occur both in skeletal and soft connective tissue, which inhibits cartilage degradation.

Resveratrol

The root of *Polygonum cuspidatum,* one of the major sources of resveratrol, has been an important constituent of Japanese and Chinese folk medicine. Resveratrol was reported to be a potent cancer chemopreventive and cardio-protective agent in vitro assays and in animal experiments. Although the precise mechanism by which resveratrol exerts its effects are unknown, a vast number of research studies may explain at least in part the basis for its anti-inflammatory actions, its favorable effects in the treatment of cardiovascular diseases and cancer (Bagchi, D, Monograph, Keats Publishing, Los Angeles, 2000). The anti-oxidant, anti-platelet aggregation and COX-2 inhibition properties along with elevation of nitric oxide production support its possible application as an anti-inflammatory agent. Resveratrol inhibits apoptosis in K562 cells through a mechanism involving inhibition of both lipooxygenase and cyclooxygenase activities (MacCarrone, M., et al., *Eur. J. Biochem.,* 265, 27-34, 1999). A study conducted at Barcelona University in Spain found resveratrol treatment of mouse macrophases inhibited COX-2 expression and dose dependently suppressed prostaglandin E2 production without affecting COX-1 protein expression (Martinez, J., et al., *Biochem. Pharmacol.,* 59, 865-870, 2000). The National Cancer Institute is currently funding clinical studies on resveratrol in healthy humans and patients with early stage cancers. It has jointly awarded a research grant totaling $ 1.7 million to University of Lichester and University of Michigan to carry out a research study for this purpose.

White Willow

White Willow (*Salix alba*) bark is a traditional analgesic and antipyretic agent. It contains bitter phenolic and flavonoid glycosides. The most active component is salicin, which is converted in the liver to acetyl salicyclic acid, an effective anti-inflammatory agent. Salicylates inhibit cyclooxygenase activity and production of prostaglandins. Clinical trials (Schmid, B., et al., *Phytother. Res.,* 15, 344-350, 2001) show that willow bark provides significant support to individuals with inflammation and pain. It is well tolerated without the gastrointestinal problems usually associated with asprin. White Willow bark extract standardized to 15% salicin is used in this study. Extracts standardized to different concentrations could also be used.

Ginger

Ginger (*Zingiber officinale*) has been used as a treatment for nausea, diarrhea and epigastric and joint pains in Ayurvedic and traditional Chinese medicine. Ginger has antihistaminic activity. Ginger's oleoresin constituents have potent inhibitory effect on the biosynthesis of proinflammatory prostaglandins and leukotrienes. Shogaol and paradol inhibit COX-2 activity and gingerol inhibits 5-LOX enzyme activity (Tjendraputra, E., et al., *Bioorg. Chem.,* 29, 156-163, 2001; Srivastava, K. C., et al., *Med. Hypoth,* 39, 342-348, 1992). In an uncontrolled trial, all seven arthritis patients treated with half gram of powdered ginger per day reported pain relief and decreased signs of inflammation (Srivastava, K. C., et al., *Med. Hypoth,* 39, 342-348, 1992). Ginger root extract standardized to 5% gingerols is used to prepare this composition. Extracts standardized to other concentrations and other components could also be used for this composition.

Quercetin

Quercetin is ubiquitous in the plant kingdom and is the most abundant among all the flavonoid compounds. Quercetin has many beneficial effects on human helath including cardiovascular protection, anticancer, antiulcer, antiallergy effects, cataract prevention, antiviral activity and anti-inflammatory effects. Its antioxidant activity may be responsible for most of its beneficial effects. Quercetin inhibits cyclooxygenases and lipooxygenases and modulate the production of inflammation causing leukotrienes and prostaglandins (Loggia, G., et. Al., *Pharmacol. Res. Commun.*, 20, S91-S94, 1988; Kim, H. P., et al., *Prostaglandins Leukot Fatty Acids*, 58, 17-24, 1998). The inhibitory actions of quercetin on histamine release from mast cell and basophils may also contribute to quercetin's anti-inflammatory activity (Fox, C. C., et al., *J. Allergy Clin Immunol*, 81, 89-94, 1988; Bronner, C., et al., *Agents Actions*, 16, 147-151, 1985). Quercetin is non-toxic. Carcinogenic and teratogenic studies in rats and rabbits have shown that it is without any apparent side affects even at the dose levels of 2000 g/kg.

Over the years, the medical establishment has witnessed that chronic inflammation is associated with increased risk of cancer development in the effected organ (Ristimaki A., *Novartis Found Symp.* 256:215-221; discussion 221-6, 259-269, 2004). Experimental and epidemiological studies demonstrated that non steroidal anti inflammatory drugs (NSAIDS) are effective in prevention of human cancers (Ristimaki A., *Novartis Found Symp.* 256:215-221; discussion 221-226, 259-269, 2004; Ratliff T L, *J Urol.*, 174(2):787-788, 2005). As the inflammatory and carcinogenesis processes are known to be triggered by increased activity of arachidonic acid (Zhi, H., et. al., *Int J Cancer.*, 106(3):327-333, 2003;), the anti-inflammatory compounds with 5-LOX and COX-2 inhibitory properties play a potential role in the prevention and treatment of cancers (Ding, X. Z., et. al., *Pancreatology.* 1(4):291-299, 2001). COX-2 and 5-LOX have thus become important targets for the prevention and treatment of cancers (Pereg D and Lishner M., J Intern Med. 258(2):115-123, 2005). Aspirin, Ibuprofen, Celecoxib, Vioxx and many other non-steroidal anti-inflammatory drugs have been proven to be effective in reducing the risk of cancer (Ratliff T L, J Urol. 174(2):787-788, 2005; Coles M and Toth B., *In Vivo.* 19(4): 661-665, 2005). Turmeric has been reported to protect humans against the development and growth of various cancers (kuttan R., et. al., Cancer Letters, 29(2): 197-202, 1985) Preclinical and clinical studies have established that resveratrol has a role in prevention and therapy of cancer (Anticancer Res. 24(5A):2783-840, 2004). Boswellic acids also exhibited antitumor activities (Jing Y., et. al., *Leukemia Research.* 23: 43-50, 1999; Bogenreider T., et. al., *Proc Am Assoc Cancer Res.* 38: 216, 1997). Quercetin and Ginger have also shown anticancer properties.

The present invention provides a new phytochemical compositions by mixing appropriate unit doses of the above phytochemicals to get the composition suitable for treating inflammatory diseases and cancer chemoprevention.

The new phytochemical compositions of the present invention may be produced by the procedures described herein or variations thereof, which will be apparent to those skilled in the art.

A further aspect of the present invention is a pharmaceutical formulation comprising a composition as described above in a pharmaceutically acceptable carrier (e.g., an aqueous or non aqueous carrier)

A still further aspect of the present invention is a method of treating inflammatory diseases or abnormal proliferation that comprises of administrating to a human or animal subject in need thereof a treatment effective amount (e.g., an amount effective to treat, slow the progression of, etc.) of a composition as described above.

The active components of the new phytochemical composition, 5-LOXIN, glucosamine salt and curcuminoids, optionally in the presence of other ingredients of the subject invention work synergistically and the composition exhibit higher potency in controlling inflammation than the individual ingredients described in this invention (table 2). The formulations-I (5-LOXIN+glucosamine salt+curcuminoids+ginger extract) and II (5-LOXIN+glucosamine salt+curcuminoids+resveratrol) showed Brine shrimp lethality in Brine shrimp assay. Brine shrimp lethality is reported to have correlation with antitumor activity (Mclaughlin, J. L., et. al., *Drug Information Journal*, 32: 513-524, 1998).

The preferred embodiments, related to the preparation of various compositions of the subject invention using appropriate doses of the selected individual ingredients, are illustrated in the following examples and summarized in table 1.

EXAMPLE 1

A composition was prepared by mixing unit doses of the following components: 5-LOXIN (300 mg), glucosamine hydrochloride (1.5 g) and curcuminoids (300 mg).

EXAMPLE 2

A composition was prepared by mixing unit doses of the following components: 5-LOXIN (200 mg), glucosamine hydrochloride (2.0 g) and curcuminoids (0.3 g).

EXAMPLE 3

A composition was prepared by mixing unit doses of the following components: 5-LOXIN (100 mg), glucosamine hydrochloride (2.0 g) and curcuminoids (400 mg).

EXAMPLE 4

A composition was prepared by mixing unit doses of the following components: 5-LOXIN (200 mg), glucosamine hydrochloride (2 g), curcuminoids (300 mg) and bromelain (400 mg).

EXAMPLE 5

A composition was prepared by mixing unit doses of the following components: 5-LOXIN (100 mg), glucosamine hydrochloride (2 g), curcuminoids (400 mg) and bromelain (400 mg).

EXAMPLE 6

A composition was prepared by mixing unit doses of the following components: 5-LOXIN (200 mg), glucosamine hydrochloride (2 g), curcuminoids (300 mg) and methylsulfonylmethane (500 mg).

EXAMPLE 7

A composition was prepared by mixing unit doses of the following components: 5-LOXIN (100 mg), glucosamine hydrochloride (2 g), curcuminoids (400 mg) and methylsulfonylmethane (500 mg).

EXAMPLE 8

A composition was prepared by mixing unit doses of the following components: 5-LOXIN (100 mg), glucosamine hydrochloride (1 g), curcuminoids (400 mg) and methylsulfonylmethane (500 mg).

EXAMPLE 9

A composition was prepared by mixing unit doses of the following components: 5-LOXIN (200 mg), glucosamine hydrochloride (2 g), curcuminoids (300 mg) and Chondroitin sulfate (200 mg).

EXAMPLE 10

A composition was prepared by mixing unit doses of the following components: 5-LOXIN (100 mg), glucosamine hydrochloride (2 g), curcuminoids (400 mg) and Chondroitin sulfate (200 mg).

EXAMPLE 11

A composition was prepared by mixing unit doses of the following components: 5-LOXIN (200 mg), glucosamine hydrochloride (2 g), curcuminoids (300 mg) and resveratrol (10 mg).

EXAMPLE 12

A composition was prepared by mixing unit doses of the following components: 5-LOXIN (100 mg), glucosamine hydrochloride (2 g), curcuminoids (400 mg) and resveratrol (10 mg).

EXAMPLE 13

A composition was prepared by mixing unit doses of the following components: 5-LOXIN (200 mg), glucosamine hydrochloride (2 g), curcuminoids (300 mg) and White willow extract (50 mg).

EXAMPLE 14

A composition was prepared by mixing unit doses of the following components: 5-LOXIN (100 mg), glucosamine hydrochloride (2 g), curcuminoids (400 mg), and White willow extract (50 mg).

EXAMPLE 15

A composition was prepared by mixing unit doses of the following components: 5-LOXIN (200 mg), glucosamine hydrochloride (2 g), curcuminoids (300 mg), and Ginger extract (40 mg).

EXAMPLE 16

A composition was prepared by mixing unit doses of the following components: 5-LOXIN (100 mg), glucosamine hydrochloride (2 g), curcuminoids (400 mg), and Ginger extract (40 mg).

EXAMPLE 17

A composition was prepared by mixing unit doses of the following components: 5-LOXIN (200 mg), glucosamine hydrochloride (2 g), curcuminoids (300 mg) and quercetin (250 mg).

EXAMPLE 18

A composition was prepared by mixing unit doses of the following components: 5-LOXIN (100 mg), glucosamine hydrochloride (2 g), curcuminoids (400 mg) and quercetin (250 mg).

EXAMPLE 19

Effect of 5-LOXIN compositions on Freund's Adjuvant-Induced Arthritis in Winstar Albino rats: Wistar Albino rats of either sex were selected randomly and divided into groups containing 6 rats (3 male and 3 female) each. The rats of treatment groups were administered orally a suspension of 5-LOXIN (15 mg/kg, p.o.) or glucosamine salt (135 mg/kg, p.o.) or curcuminoids (20 mg/kg, p.o.) or ginger (3 mg/kg, p.o.) or one fifth of a formulation containing unit doses of all the four ingredients [formulation I: 5-LOXIN (15 mg)+glucosamine (135 mg)+curcuminoids DP 95% (20 mg)+Ginger DP 15% total pungent compounds (3 mg)]or prednisolone (10 mg/kg, p.o.) in 0.5% CMC, for 30 days. The control group received 0.5% CMC. Following the drug treatment all animals were challenged, on $31^{st}$ day, with 50 µl of complete Freund's adjuvant injection to the sub plantar region of right hind paw. The paw volume was measured before ($V_0$) and after the injection of Freund's adjuvant at the end of 30, 60, 120, 180, 240 and 360 min by Plethysmograph. The paw oedema was measured everyday upto $17^{th}$ day. The degree of inflammatory response on $13^{th}$ day was used for comparison as suggested by Pearson et al. The results are summarized in table 2.

EXAMPLE 20

Brine shrimp lethality assay: Brine shrimp lethality (BSL) assay is a simple bench top bioassay developed by McLaughlin, et. al. (*Studies in Natural Product Chemistry*, 9, page 383, 1991 and *Am. Chem. Soc. Symp. Series*, 534, page 114, 1992) and the results obtained by this assay have been reported to be corroborative with the cytotoxicities determined in 9KB and 9PS cells. The procedure involves hatching *Artemia salina* cysts in a cone shaped vessel and collecting active nauplii after 48 hr and treating with a range of known concentrations of test substances and vehicle (control) in tubes each tube containing 10 nauplii and checking viability/mortality after 24 hr. Percentage lethality was calculated by comparing mean values of control and test sets of three tubes each. $LC_{50}$ values were obtained from the graph plotted micro molar concentration against percent lethality. The formulation-I and formulation II [5-LOXIN (15 mg)+glucosamine (135 mg)+curcuminoids DP 95% (20 mg)+resveratrol (10 mg)] showed 50% inhibition of Brine shrimp cultures ($LC_{50}$) at concentrations 31.8 µg/mL and 28 µg/mL respectively.

Even though, a single optional ingredient has been used in each of the above examples, more than one optional ingredient can also be selected per combination to produce new compositions.

Though the above examples describe selected embodiments of this invention, obvious equivalents and modifications known to the persons skilled in the art are not excluded from the scope of the present invention.

The claimed dietary supplement is useful for the treatment of inflammatory diseases. The claimed dietary supplement is also useful as an anticancer agent and as an antioxidant.

TABLE 1

5-LOXIN COMBINATIONS

| S. No | 5-LOXIN | Glucosamine Hydrochloride | Curcuminoids | Optional ingredient wt | name |
|---|---|---|---|---|---|
| 1 | 300 mg | 1.5 g | 300 mg | | |
| 2 | 200 mg | 2.0 g | 300 mg | | |
| 3 | 100 mg | 2.0 g | 400 mg | | |
| 4 | 200 mg | 2.0 g | 300 mg | 400 mg | bromelain |
| 5 | 100 mg | 2.0 g | 400 mg | 400 mg | bromelain |
| 6 | 200 mg | 2.0 g | 300 mg | 500 mg | MSM |
| 7 | 100 mg | 2.0 g | 400 mg | 500 mg | MSM |
| 8 | 100 mg | 1.0 g | 400 mg | 500 mg | MSM |
| 9 | 200 mg | 2.0 g | 300 mg | 200 mg | Chondroitin |
| 10 | 100 mg | 2.0 g | 400 mg | 200 mg | Chondroitin |
| 11 | 200 mg | 2.0 g | 300 mg | 10 mg | Resveratrol |
| 12 | 100 mg | 2.0 g | 400 mg | 10 mg | Resveratrol |
| 13 | 200 mg | 2.0 g | 300 mg | 50 mg | White Willow |
| 14 | 100 mg | 2.0 g | 400 mg | 50 mg | White Willow |
| 15 | 200 mg | 2.0 g | 300 mg | 40 mg | Ginger |
| 16 | 100 mg | 2.0 g | 400 mg | 40 mg | Ginger |
| 17 | 200 mg | 2.0 g | 300 mg | 250 mg | Quercetin |
| 18 | 100 mg | 2.0 g | 400 mg | 250 mg | Quercetin |

TABLE 2

PROTECTIVE EFFECT OF INDIVIDUAL INGREDIENTS AND COMBINATION ON ADJUVANT INDUCED ARTHRITIS

| Rat ID | Test samples | DOSE mg/ml | Paw Volume In ML After Freund"s Adjuvant | | | % protection |
|---|---|---|---|---|---|---|
| | | | 0 hr | Day-13 PV | E | |
| M04281 | CONTROL | | 1.11 | 1.72 | 0.61 | |
| M04292 | | | 1.13 | 1.68 | 0.55 | |
| M04303 | | | 1.33 | 1.68 | 0.35 | |
| M04313 | | | 1.43 | 1.75 | 0.32 | |
| M04315 | | | 1.18 | 1.74 | 0.56 | |
| | | | | ME/SEM | 0.478 | 0.054 |
| M04282 | 5-LOXIN | 15 | 1.22 | 1.5 | 0.28 | 43.51 |
| M04293 | | | 1.32 | 1.59 | 0.27 | |
| M04304 | | | 1.34 | 1.6 | 0.26 | |
| | | | | ME/SEM | 0.27 | 0.006 |
| M04283 | Glucosamine | 135 | 1.19 | 1.56 | 0.37 | 37.94 |
| M04294 | | | 1.29 | 1.59 | 0.3 | |
| M04305 | | | 1.31 | 1.53 | 0.22 | |
| | | | | ME/SEM | 0.30 | 0.043 |
| M04284 | curcuminoidsDP | 20 | 1.36 | 1.64 | 0.28 | 30.96 |
| M04295 | 95% | | 1.19 | 1.64 | 0.45 | |
| M04311 | | | 1.34 | 1.6 | 0.26 | |
| | | | | ME/SEM | 0.33 | 0.060 |
| M04285 | Ginger 15% DP | 3 | 1.22 | 1.56 | 0.34 | 38.63 |
| M04301 | | | 1.29 | 1.58 | 0.29 | |
| M04312 | | | 1.38 | 1.63 | 0.25 | |
| | | | | ME/SEM | 0.29 | 0.026 |
| M04291 | Formulation-I | 35 | 1.29 | 1.67 | 0.38 | 42.12 |
| M04302 | | | 1.34 | 1.56 | 0.22 | |
| M04314 | | | 1.39 | 1.62 | 0.23 | |
| | | | | ME/SEM | 0.28 | 0.052 |

The invention claimed is:

1. A phytochemical dietary supplement and therapeutic composition capable of treating and controlling inflammatory diseases and cancer comprising: 2-30% by weight of a standardized *Boswellia serrata* extract containing at least 30% of 3-O-acetyl-11-keto-β-boswellic acid (AKBA); glucosamine salt and 5-30% by weight of curcuminoid salt; and the composition optionally containing bromelain, chondroitin, methylsulphonylmethane, resveratrol, extracts of white Willow and ginger, and quercetin.

2. The composition of claim 1, wherein the standardized *Boswellia serrata* extract contains 30% of AKBA.

3. The composition of claim 1, wherein said glucosamine salt is selected from glucosamine hydrochloride, glucosamine sulphate and N-acetyl glucosamine.

4. The composition of claim 1, containing 2-25% by weight of the standardized *Boswellia serrata* extract, glucosamine salt, 5-25% by weight of curcuminoid salt and 5-25% by weight of bromelain.

5. The composition of claim 1, containing 2-25% by weight of the standardized *Boswellia serrata* extract, glucosamine salt, 5-25% by weight of curcuminoid salt and 5-25% by weight of methylsulphonylmethane.

6. The composition of claim 1, containing 2-25% by weight of the standardized *Boswellia serrata* extract, glucosamine salt, 10-25% by weight of curcuminoid salt and 0.2-10% by weight of resveratrol.

7. The composition of claim 1, containing 2-25% by weight of the standardized *Boswellia serrata* extract, glucosamine salt, 5-25% by weight of curcuminoid salt and 5-25% by weight of chondroitin sulphate.

8. The composition of claim 1, containing 2-25% by weight of the standardized *Boswellia serrata* extract, glucosamine salt, 8-25% by weight of curcuminoid salt and 1-10% by weight of white willow extract.

9. The composition of claim 1, containing 2-25% by weight of the standardized *Boswellia serrata* extract, glucosamine salt, 8-25% by weight of curcuminoid salt and 1-10% by weight of ginger extract.

10. The composition of claim 1, containing 2-25% by weight of the standardized *Boswellia serrata* extract, glucosamine salt, 5-25% by weight of curcuminoid salt and 5-25% by weight of quercetin.

11. A dietary, nutraceutical and pharmaceutical formulation containing the composition of claim 1 in admixture with known pharmaceutically acceptable adjuvants diluents and carriers.

12. The composition of claim 1, wherein the *Boswellia serrata* extract contains 40% of AKBA.

13. The composition of claim 1, wherein the standardized *Boswellia serrata* extract contains more than 30% of AKBA.

14. The composition of claim 1, wherein the standardized *Boswellia serrata* extract contains more than 40% of AKBA.

* * * * *